(12) United States Patent
Kurahashi

(10) Patent No.: US 8,802,593 B2
(45) Date of Patent: Aug. 12, 2014

(54) COMPOSITION AND METHOD FOR CONTROLLING PLANT DISEASES

(75) Inventor: Makoto Kurahashi, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/321,588

(22) PCT Filed: May 21, 2010

(86) PCT No.: PCT/JP2010/059052
§ 371 (c)(1),
(2), (4) Date: Jan. 18, 2012

(87) PCT Pub. No.: WO2010/137673
PCT Pub. Date: Dec. 2, 2010

(65) Prior Publication Data
US 2012/0122677 A1    May 17, 2012

(30) Foreign Application Priority Data
May 25, 2009 (JP) ................................. 2009-125900

(51) Int. Cl.
| | | |
|---|---|---|
| *A01N 37/18* | (2006.01) | |
| *A01N 37/38* | (2006.01) | |
| *A01N 37/30* | (2006.01) | |
| *A01N 37/50* | (2006.01) | |
| *A01N 43/54* | (2006.01) | |
| *A01N 43/56* | (2006.01) | |
| *A01N 47/12* | (2006.01) | |
| *A01N 47/24* | (2006.01) | |
| *A01P 3/00* | (2006.01) | |

(52) U.S. Cl.
USPC ........... 504/100; 514/269; 514/407; 514/479; 514/539; 514/563; 514/622

(58) Field of Classification Search
USPC ................. 514/563, 269, 407, 479, 539, 622; 504/100
See application file for complete search history.

(56) References Cited

U.S. PATENT DOCUMENTS

| 5,948,819 | A | 9/1999 | Ohtsuka et al. |
| 6,313,150 | B1 | 11/2001 | Ohtsuka et al. |
| 2002/0065228 | A1 | 5/2002 | Linderman et al. |
| 2004/0248955 | A1 | 12/2004 | Wachendorff-Neumann et al. |
| 2009/0111698 | A1* | 4/2009 | Silverman et al. ............. 504/321 |
| 2010/0267565 | A1* | 10/2010 | Kurahashi et al. ............. 504/322 |

FOREIGN PATENT DOCUMENTS

| JP | 59-39803 | 3/1984 |
| JP | 11-255607 | 9/1999 |
| JP | 2005-524603 | 8/2005 |
| JP | 4087942 | 2/2008 |
| WO | 95/27693 | 10/1995 |
| WO | 99/45774 | 9/1999 |
| WO | 2009/055044 | 4/2009 |
| WO | 2010/123849 | 10/2010 |

OTHER PUBLICATIONS

Extended European Search Report issued Feb. 4, 2013 in corresponding European Application No. 10780627.5.
Mueller, D., "Fungicides: QoI fungicides", Integrated Crop Management, May 2006, p. 129, retrieved Jan. 23, 2013 from http://www.ipm.iastate.edu/ipm/icm/2006/5-22/fungicides.html.
Bartlett, Dave W., et al., "Review: The strobilurin fungicides", Pest Manag. Sci., vol. 58, 2002, pp. 649-662.
Itagaki, Mihoko, et al., "Biological activities and structure-activity relationship of substitution compounds of N-[2-(3-indolyl)ethyl]succinamic acid and N[2-(1-naphthyl)ethyl]succinamic acid, derived from a new category of root-promoting substances, N-(phenethyl)succinamic acid analogs", Plant and Soil, vol. 255, 2003, pp. 67-75.
Chinese Office Action issued Apr. 16, 2013 in corresponding Chinese Application No. 201080024919.4 with English translation.
Colombian Office Action issued May 16, 2013 in corresponding Colombian Application No. 11-161346 with English abstract.
Letter dated Jun. 13, 2013 from foreign associate forwarding Colombian Office Action.
C. D. S. Tomlin ; "A World Compendium: The Pesticide Manual—Fourteenth Edition"; British Crop Protection Council (BCPC); ISBN 1901396142; pp. 54-56, 351, 499, 500, 636, 637, 719, 720, 842, 843, 900, 901, 982, 1074, 1075, 1284-1299, 1306, 1314, 1325, 1328, 1335 and 1339.
Chinese Office Action issued Nov. 4, 2013 in corresponding Chinese Application No. 201080024919.4 (with English translation).
International Search Report issued Jul. 6, 2010 in International (PCT) Application No. PCT/JP2010/059052 along with the Written Opinion.

* cited by examiner

*Primary Examiner* — John Pak
(74) *Attorney, Agent, or Firm* — Wenderoth, Lind & Ponack, L.L.P.

(57) ABSTRACT

The present invention provides: a composition for controlling plant diseases comprising, as active ingredients, 4-oxo-4-[(2-phenylethyl)amino]-butyric acid and a quinone outside inhibitor; a method for controlling plant diseases which comprises applying effective amounts of 4-oxo-4-[(2-phenylethyl)amino]-butyric acid and a quinone outside inhibitor to a plant or soil for growing plant; and so on.

5 Claims, No Drawings

COMPOSITION AND METHOD FOR CONTROLLING PLANT DISEASES

This application is a U.S. national stage of International Application No. PCT/JP2010/059052 filed May 21, 2010.

TECHNICAL FIELD

The present invention relates to a composition for controlling plant diseases and a method for controlling plant diseases.

BACKGROUND ART

As an active ingredient for a plant growth regulator, 4-oxo-4-[(2-phenylethyl)amino]-butyric acid has been known (Japanese Patent No. 4,087,942). Quinone outside Inhibitors (hereinafter, referred to as QoI in some cases) have been known as active ingredients of agents for controlling plant diseases (WO 95/27693; The Pesticide Manual-14th edition, published by British Crop Protection Council (BCPC), ISBN1901396142).

DISCLOSURE OF INVENTION

An object of the present invention is to provide a composition for controlling plant diseases and a method for controlling plant diseases, having excellent control efficacy for plant diseases.

The present invention provides a composition for controlling plant diseases and a method for controlling plant diseases, in which control efficacy for plant diseases has been increased by the combined use of 4-oxo-4-[(2-phenylethyl)amino]-butyric acid and QoI.

Specifically, the present invention takes the following constitutions:

[1] A composition for controlling plant diseases comprising, as active ingredients, 4-oxo-4-[(2-phenylethyl)amino]-butyric acid and a quinone outside inhibitor;

[2] The composition according to [1], wherein the quinone outside inhibitor is at least one quinone outside inhibitor selected from the group consisting of kresoxim-methyl, azoxystrobin, trifloxystrobin, fluoxastrobin, picoxystrobin, pyraclostrobin, dimoxystrobin, pyribencarb, metominostrobin, orysastrobin, enestrobin, and a compound of formula (1):

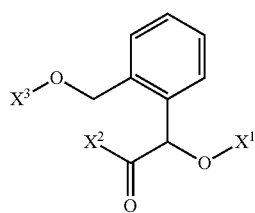

(1)

wherein $X^1$ represents a methyl group, a difluoromethyl group or an ethyl group; $X^2$ represents a methoxy group or a methylamino group; and $X^3$ represents a phenyl group, a 2-methylphenyl group or a 2,5-dimethylphenyl group;

[3] The composition according to [1], wherein a weight ratio of 4-oxo-4-[(2-phenylethyl)amino]-butyric acid to the quinone outside inhibitor is in the range of 0.005:1 to 1000:1;

[4] A seed treatment agent comprising, as active ingredients, 4-oxo-4-[(2-phenylethyl)amino]-butyric acid and a quinone outside inhibitor;

[5] A plant seed treated with effective amounts of 4-oxo-4-[(2-phenylethyl)amino]-butyric acid and a quinone outside inhibitor;

[6] A method for controlling plant diseases which comprises applying effective amounts of 4-oxo-4-[(2-phenylethyl)amino]-butyric acid and a quinone outside inhibitor to a plant or soil for growing plant; and

[7] Combined use for controlling plant diseases of 4-oxo-4-[(2-phenylethyl)amino]-butyric acid and a quinone outside inhibitor; and so on.

The composition of the present invention exhibits an excellent control efficacy for plant diseases.

MODES FOR CARRYING OUT THE INVENTION

One of the compounds for use in the composition for controlling plant diseases of the present invention is 4-oxo-4-[(2-phenylethyl)amino]-butyric acid (hereinafter, referred to as the compound I in some cases), which is a compound disclosed in Japanese Patent No. 4,087,942 and can be produced, for example, by the method described in the patent publication.

The compound I, 4-oxo-4-[(2-phenylethyl)amino]-butyric acid, may be a salt with a base. Examples of the basic salt of 4-oxo-4-[(2-phenylethyl)amino]-butyric acid include the followings:

metal salts such as alkali metal salts and alkali earth metal salts, including salts of sodium, potassium or magnesium;
salts with ammonia; and
salts with organic amines such as morpholine, piperidine, pyrrolidine, mono lower alkylamine, di lower alkylamine, tri lower alkylamine, monohydroxy lower alkylamine, dihydroxy lower alkylamine and trihydroxy lower alkylamine.

Examples of the QoI for use in the composition for controlling plant diseases of the present invention include at least one quinone outside inhibitor selected from the group consisting of kresoxim-methyl, azoxystrobin, trifloxystrobin, fluoxastrobin, picoxystrobin, pyraclostrobin, dimoxystrobin, pyribencarb, metominostrobin, orysastrobin, enestrobin, and the compound of formula (1). These QoIs are compounds known in the art and disclosed at pages 54, 351, 499, 636, 719, 842, 900, 982 and 1074 of "the Pesticide Manual-14th edition" published by British Crop Protection Council (BCPC), ISBN1901396142; or in WO 95/27693. These QoIs can be obtained from commercial agents or prepared using methods known in the art.

The compound of formula (1) of the QoIs for use in the composition for controlling plant diseases of the present invention is described.

Examples of the compound of formula (1) include the following compounds:

a compound in which $X^1$ is a methyl group, a difluoromethyl group or an ethyl group in formula (1);

a compound in which $X^1$ is a methyl group in formula (1);

a compound in which $X^2$ is a methoxy group or a methylamino group in formula (1);

a compound in which $X^1$ is a methyl group and $X^2$ is a methoxy group in formula (1);

a compound in which $X^1$ is a methyl group and $X^2$ is methylamino group in formula (1);

a compound in which $X^3$ is a phenyl group, a 2-methylphenyl group or a 2,5-dimethylphenyl group in formula (1);

a compound in which $X^3$ is a phenyl group or a 2,5-dimethylphenyl group in formula (1);

a compound in which $X^1$ is a methyl group, $X^2$ is a methoxy group, and $X^3$ is a 2,5-dimethylphenyl group in formula (1);

a compound in which X¹ is a methyl group, X² is methylamino group, and X³ is a phenyl group in formula (1); and a compound in which X¹ is a methyl group, X² is methylamino group, and X³ is a 2,5-dimethylphenyl group in formula (1).

Specific examples of the compound of formula (1) are shown.

In the compound of formula (1), X¹, X² and X³ are one of the combinations of members shown in Table 1.

TABLE 1

| $X^1$ | $X^2$ | $X^3$ |
|---|---|---|
| $CH_3$ | $OCH_3$ | Ph |
| $CH_3$ | $OCH_3$ | $2\text{-}CH_3Ph$ |
| $CH_3$ | $OCH_3$ | $2,5\text{-}(CH_3)_2Ph$ |
| $CH_3$ | $NHCH_3$ | Ph |
| $CH_3$ | $NHCH_3$ | $2\text{-}CH_3Ph$ |
| $CH_3$ | $NHCH_3$ | $2,5\text{-}(CH_3)_2Ph$ |
| $CHF_2$ | $OCH_3$ | Ph |
| $CHF_2$ | $OCH_3$ | $2\text{-}CH_3Ph$ |
| $CHF_2$ | $OCH_3$ | $2,5\text{-}(CH_3)_2Ph$ |
| $CHF_2$ | $NHCH_3$ | Ph |
| $CHF_2$ | $NHCH_3$ | $2\text{-}CH_3Ph$ |
| $CHF_2$ | $NHCH_3$ | $2,5\text{-}(CH_3)_2Ph$ |
| $C_2H_5$ | $OCH_3$ | Ph |
| $C_2H_5$ | $OCH_3$ | $2\text{-}CH_3Ph$ |
| $C_2H_5$ | $OCH_3$ | $2,5\text{-}(CH_3)_2Ph$ |
| $C_2H_5$ | $NHCH_3$ | Ph |
| $C_2H_5$ | $NHCH_3$ | $2\text{-}CH_3Ph$ |
| $C_2H_5$ | $NHCH_3$ | $2,5\text{-}(CH_3)_2Ph$ |

The compound of formula (1) may have isomers such as tautomers and stereoisomers including optical isomers based on an asymmetric carbon atoms, and any isomer can be contained and used singly or in a mixture of any isomer ratio in the present invention.

The compound of formula (1) may be in a form of a solvate (for example, hydrate) and it can be used in a form of a solvate in the present invention.

The compound of formula (1) may be in a form of a crystal form and/or an amorphous form and it can be used in any form in the present invention.

The compound of formula (1) is a compound described in WO95/27,693 pamphlet. These compounds can be synthesized, for example, by a method described in the pamphlet.

In the composition for controlling plant diseases of the present invention, the weight ratio of the compound I to QoI is typically in the range of 0.005:1 to 1000:1, preferably 0.02:1 to 500:1. When applied as a foliar spray, the weight ratio is typically in the range of 0.005:1 to 1000:1, preferably 0.02:1 to 500:1. When used as a seed treatment agent, the weight ratio is typically in the range of 0.02:1 to 500:1, preferably 0.1:1 to 200:1.

The composition for controlling plant diseases of the present invention may be a simple mixture of the compound I and QoI. Alternatively, the composition for controlling plant diseases is typically produced by mixing the compound I and QoI with an inert carrier, and adding to the mixture a surfactant and other adjuvants as needed so that the mixture can be formulated into an oil agent, an emulsion, a flowable agent, a wettable powder, a granulated wettable powder, a powder agent, a granule agent and so on. The composition for controlling plant diseases mentioned above can be used as a seed treatment agent as it is or added with other inert ingredients.

In the composition for controlling plant diseases of the present invention, the total amount of the compound I and QoI is typically in the range of 0.1 to 99% by weight, preferably 0.2 to 90% by weight.

Examples of the solid carrier used in formulation include fine powders or granules such as minerals such as kaolin clay, attapulgite clay, bentonite, montmorillonite, acid white clay, pyrophyllite, talc, diatomaceous earth and calcite; natural organic materials such as corn rachis powder and walnut husk powder; synthetic organic materials such as urea; salts such as calcium carbonate and ammonium sulfate; synthetic inorganic materials such as synthetic hydrated silicon oxide; and as a liquid carrier, aromatic hydrocarbons such as xylene, alkylbenzene and methylnaphthalene; alcohols such as 2-propanol, ethyleneglycol, propylene glycol, and ethylene glycol monoethyl ether; ketones such as acetone, cyclohexanone and isophorone; vegetable oil such as soybean oil and cotton seed oil; petroleum aliphatic hydrocarbons, esters, dimethylsulfoxide, acetonitrile and water.

Examples of the surfactant include anionic surfactants such as alkyl sulfate ester salts, alkylaryl sulfonate salts, dialkyl sulfosuccinate salts, polyoxyethylene alkylaryl ether phosphate ester salts, lignosulfonate salts and naphthalene sulfonate formaldehyde polycondensates; and nonionic surfactants such as polyoxyethylene alkyl aryl ethers, polyoxyethylene alkylpolyoxypropylene block copolymers and sorbitan fatty acid esters and cationic surfactants such as alkyltrimethylammonium salts.

Examples of the other formulation auxiliary agents include water-soluble polymers such as polyvinyl alcohol and polyvinylpyrrolidone, polysaccharides such as Arabic gum, alginic acid and the salt thereof, CMC (carboxymethyl-cellulose), Xanthan gum, inorganic materials such as aluminum magnesium silicate and alumina sol, preservatives, coloring agents and stabilization agents such as PAP (acid phosphate isopropyl) and BHT.

The composition for controlling plant diseases of the present invention is effective for the following plant diseases.

Diseases of rice: blast (*Magnaporthe grisea*), Helminthosporium leaf spot (*Cochliobolus miyabeanus*), sheath blight (*Rhizoctonia solani*), and bakanae disease (*Gibberella fujikuroi*).

Diseases of wheat: powdery mildew (*Erysiphe graminis*), Fusarium head blight (*Fusarium graminearum, F. avenacerum, F. culmorum, Microdochium nivale*), rust (*Puccinia striiformis, P. graminis, P. recondita*), pink snow mold (*Micronectriella nivale*), Typhula snow blight (*Typhula* sp.), loose smut (*Ustilago tritici*), bunt (*Tilletia caries*), eyespot (*Pseudocercosporella herpotrichoides*), leaf blotch (*Mycosphaerella graminicola*), glume blotch (*Stagonospora nodorum*), and yellow spot (*Pyrenophora tritici-repentis*).

Diseases of barley: powdery mildew (*Erysiphe graminis*), Fusarium head blight (*Fusarium graminearum, F. avenacerum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), and Rhizoctonia damping-off (*Rhizoctonia solani*).

Diseases of corn: smut (*Ustilago maydis*), brown spot (*Cochliobolus heterostrophus*), copper spot (*Gloeocercospora sorghi*), southern rust (*Puccinia polysora*), gray leaf spot (*Cercospora zeae-maydis*), and Rhizoctonia damping-off (*Rhizoctonia solani*).

Diseases of citrus: melanose (*Diaporthe citri*), scab (*Elsinoe fawcetti*), penicillium rot (*Penicillium digitatum, P. italicum*), and brown rot (*Phytophthora parasitica, Phytophthora citrophthora*).

Diseases of apple: blossom blight (*Monilinia mali*), canker (*Valsa ceratosperma*), powdery mildew (*Podosphaera leucotricha*), Alternaria leaf spot (*Alternaria alternata* apple pathotype), scab (*Venturia inaequalis*), bitter rot (*Colletotrichum acutatum*), crown rot (*Phytophtora cactorum*), blotch (*Diplocarpon mali*), ring rot (*Botryosphaeria berengeriana*), and violet root rot (*Helicobasidium mompa*).

Diseases of pear: scab (*Venturia nashicola, V. pirina*), black spot (*Alternaria alternata* Japanese pear pathotype), rust (*Gymnosporangium haraeanum*), and *phytophthora* fruit rot (*Phytophtora cactorum*).

Diseases of peach: brown rot (*Monilinia fructicola*), scab (*Cladosporium carpophilum*), and *phomopsis* rot (*Phomopsis* sp.).

Diseases of grape: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*).

Diseases of Japanese persimmon: anthracnose (*Gloeosporium kaki*), and leaf spot (*Cercospora kaki, Mycosphaerella nawae*).

Diseases of gourd: anthracnose (*Colletotrichum lagenarium*), powdery mildew (*Sphaerotheca fuliginea*), gummy stem blight (*Mycosphaerella melonis*), *Fusarium* wilt (*Fusarium oxysporum*), downy mildew (*Pseudoperonospora cubensis*), *Phytophthora* rot (*Phytophthora* sp.), and damping-off (*Pythium* sp.).

Diseases of tomato: early blight (*Alternaria solani*), leaf mold (*Cladosporium fulvum*), and late blight (*Phytophthora infestans*).

Diseases of eggplant: brown spot (*Phomopsis vexans*), and powdery mildew (*Erysiphe cichoracearum*).

Diseases of cruciferous vegetables: *Alternaria* leaf spot (*Alternaria japonica*), white spot (*Cercosporella brassicae*), clubroot (*Plasmodiophora brassicae*), and downy mildew (*Peronospora parasitica*).

Diseases of welsh onion: rust (*Puccinia allii*), and downy mildew (*Peronospora destructor*).

Diseases of soybean: purple seed stain (*Cercospora kikuchii*), sphaceloma scad (*Elsinoe glycines*), pod and stem blight (*Diaporthe phaseolorum* var. *sojae*), *septoria* brown spot (*Septoria glycines*), frogeye leaf spot (*Cercospora sojina*), rust (*Phakopsora pachyrhizi*), brown stem rot (*Phytophthora sojae*), and *Rhizoctonia* damping-off (*Rhizoctonia solani*).

Diseases of kidney bean: anthracnose (*Colletotrichum lindemthianum*).

Diseases of peanut: leaf spot (*Cercospora personata*), brown leaf spot (*Cercospora arachidicola*) and southern blight (*Sclerotium rolfsii*).

Diseases of garden pea: powdery mildew (*Erysiphe pisi*), and root rot (*Fusarium solani* f. sp. *pisi*).

Diseases of potato: early blight (*Alternaria solani*), late blight (*Phytophthora infestans*), pink rot (*Phytophthora erythroseptica*), powdery scab (*Spongospora* subterranean f. sp. *subterranea*), and black scurf (*Rhizoctonia solani*).

Diseases of strawberry: powdery mildew (*Sphaerotheca humuli*), and anthracnose (*Glomerella cingulata*).

Diseases of tea: net blister blight (*Exobasidium reticulatum*), white scab (*Elsinoe leucospila*), gray blight (*Pestalotiopsis* sp.), and anthracnose (*Colletotrichum theaesinensis*).

Diseases of tobacco: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*).

Diseases of rapeseed: *sclerotinia* rot (*Sclerotinia sclerotiorum*), and *Rhizoctonia* damping-off (*Rhizoctonia solani*).

Diseases of cotton: *Rhizoctonia* damping-off (*Rhizoctonia solani*).

Diseases of sugar beet: *Cercospora* leaf spot (*Cercospora beticola*), leaf blight (*Rhizoctonia solani*), Root rot (*Rhizoctonia solani*), and *Aphanomyces* root rot (*Aphanomyces cochlioides*).

Diseases of rose: black spot (*Diplocarpon rosae*), powdery mildew (*Sphaerotheca pannosa*), and downy mildew (*Peronospora sparsa*).

Diseases of chrysanthemum and asteraceous plants: downy mildew (*Bremia lactucae*), leaf blight (*Septoria chrysanthemiindici*), and white rust (*Puccinia horiana*).

Diseases of various groups: diseases caused by *Pythium* spp. (*Pythium aphanidermatum, Pythium debarianum, Pythium graminicola, Pythium irregulare, Pythium ultimum*), gray mold (*Botrytis cinerea*), *Sclerotinia* rot (*Sclerotinia sclerotiorum*), and southern blight (*Sclerotium rolfsii*).

Disease of Japanese radish: *Alternaria* leaf spot (*Alternaria brassicicola*).

Diseases of turfgrass: dollar spot (*Sclerotinia homeocarpa*), and brown patch and large patch (*Rhizoctonia solani*).

Disease of banana: sigatoka (*Mycosphaerella fijiensis, Mycosphaerella musicola*).

Disease of sunflower: downy mildew (*Plasmopara halstedii*).

Seed diseases or diseases in the early stages of the growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp. and *Diplodia* spp.

Viral diseases of various plants mediated by *Polymixa* spp. or *Olpidium* spp. and so on.

Among the above, examples of the diseases for which highly effective control of the present invention is expected include *Rhizoctonia* damping-off (*Rhizoctonia solani*) of wheat, corn, rice, soybean, cotton, rapeseed, sugar beet and turfgrass, seed diseases and diseases in the early stages of the growth of wheat, barley, corn, cotton, soybean, rapeseed and turfgrass caused by *Fusarium* spp., blast (*Magnaporthe grisea*) and bakanae disease (*Gibberella fujikuroi*) of rice, pink snow mold (*Micronectriella nivale*), powdery mildew (*Erysiphe graminis*), *Fusarium* head blight (*Fusarium graminearum, F. avenacerum, F. culmorum, Microdochium nivale*), eyespot (*Pseudocercosporella herpotrichoides*) and leaf blotch (*Mycosphaerella graminicola*) of wheat, powdery mildew (*Erysiphe graminis*), *Fusarium* head blight (*Fusarium graminearum, F. avenacerum, F. culmorum, Microdochium nivale*), rust (*Puccinia striiformis, P. graminis, P. hordei*), loose smut (*Ustilago nuda*), scald (*Rhynchosporium secalis*) and net blotch (*Pyrenophora teres*) of barley, smut (*Ustilago maydis*), southern rust (*Puccinia polysora*) and gray leaf spot (*Cercospora zeae-maydis*) of corn, *sclerotinia* rot (*Sclerotinia sclerotiorum*) of rapeseed, brown patch and large patch (*Rhizoctonia solani*) and dollar spot (*Sclerotinia homeocarpa*) of turfgrass, rust (*Phakopsora pachyrhizi*) and purple seed stain (*Cercospora kikuchii*) of soybean, *Cercospora* leaf spot (*Cercospora beticola*), leaf blight (*Thanatephorus cucumeris*), Root rot (*Thanatephorus cucumeris*) and *Aphanomyces* root rot (*Aphanomyces cochlioides*) of sugar beet, black scurf (*Rhizoctonia solani*) of potato, and sigatoka (*Mycosphaerella fijiensis, Mycosphaerella musicola*) of banana.

Plant diseases can be controlled by applying effective amounts of the compound I and QoI to the plant pathogens or to such a place as plant and soil where the plant pathogens inhabit or may inhabit.

Plant diseases can be controlled by applying effective amounts of the compound I and QoI to a plant or soil for growing plant. Examples of a plant which is the object of the application include foliages of plant, seeds of plant, bulbs of plant. As used herein, the bulb means a bulb, corm, rhizoma, stem tuber, root tuber and rhizophore.

When the application is conducted to plant pathogens, a plant or the soil for growing plant, the compound I and QoI may be separately applied for the same period, but they are typically applied as a composition for controlling plant diseases of the present invention for simplicity of the application.

Examples of the controlling method of the present invention include treatment of foliage of plants, such as foliage application; treatment of cultivation lands of plants, such as soil treatment; treatment of seeds, such as seed sterilization and seed coating; and treatment of bulbs such as seed tuber.

Examples of the treatment of foliage of plants in the controlling method of the present invention include treatment methods of applying to surfaces of plants, such as foliage spraying and trunk spraying. Examples of the treatment method of directly absorbing to plants before transplantation include a method of soaking entire plants or roots. A formulation obtained by using a solid carrier such as a mineral powder may be adhered to the roots.

Examples of the soil treatment method in the controlling method of the present invention include spraying onto the soil, soil incorporation, and perfusion of a chemical liquid into the soil (irrigation of chemical liquid, soil injection, and dripping of chemical liquid). Examples of the place to be treated include planting hole, furrow, around a planting hole, around a furrow, entire surface of cultivation lands, the parts between the soil and the plant, area between roots, area beneath the trunk, main furrow, growing soil, seedling raising box, seedling raising tray and seedbed. Examples of the treating period include before seeding, at the time of seeding, immediately after seeding, raising period, before settled planting, at the time of settled planting, and growing period after settled planting. In the above soil treatment, active ingredients may be simultaneously applied to the plant, or a solid fertilizer such as a paste fertilizer containing active ingredients may be applied to the soil. Also active ingredients may be mixed in an irrigation liquid, and, examples thereof include injecting to irrigation facilities such as irrigation tube, irrigation pipe and sprinkler, mixing into the flooding liquid between furrows and mixing into a water culture medium. Alternatively, an irrigation liquid is mixed with active ingredients in advance and, for example, used for treatment by an appropriate irrigating method including the irrigating method mentioned above and the other methods such as sprinkling and flooding.

Examples of the method of treating seeds or bulbs in the controlling method of the present invention include a method for treating seeds or bulbs to be protected from plant diseases with the composition for controlling plant diseases of the present invention and specific examples thereof include a spraying treatment in which a suspension of the composition for controlling plant diseases of the present invention is atomized and sprayed on the seed surface or the bulb surface; a smearing treatment in which a wettable powder, an emulsion or a flowable agent of the composition for controlling plant diseases of the present invention is applied to seeds or bulbs with a small amount of water added or without dilution; an immersing treatment in which seeds are immersed in a solution of the composition for controlling plant diseases of the present invention for a certain period of time; film coating treatment; and pellet coating treatment.

When foliage of a plant or soil is treated with the compound I and QoI, the amounts of the compound I and QoI used for the treatment may be changed depending on the kind of the plant to be treated, the kind and the occurring frequency of the diseases to be controlled, formulation form, treatment period, climatic condition and so on, but the total amount of the compound I and QoI (hereinafter referred to as the amount of the active ingredients) per 10,000 m$^2$ is typically 1 to 10,000 g and preferably 2 to 1,000 g.

The emulsion, wettable powder and flowable agent are typically diluted with water, and then sprinkled for the treatment. In these case, the total concentration of the compound I and QoI is typically in the range of 0.0001 to 3% by weight and preferably 0.0005 to 1% by weight. The powder agent and granule agent are typically used for the treatment without being diluted.

In the treatment of seeds, the amount of the active ingredients to be applied is typically in the range of 0.001 to 10 g, preferably 0.01 to 3 g per 1 kg of seeds.

The control method of the present invention can be used in agricultural lands such as fields, paddy fields, lawns and orchards or in non-agricultural lands.

The present invention can be used to control diseases in agricultural lands for cultivating the following "plant" and the like without adversely affecting the plant and so on.

Examples of the crops are as follows:

crops: corn, rice, wheat, barley, rye, oat, sorghum, cotton, soybean, peanut, buckwheat, beet, rapeseed, sunflower, sugar cane, tobacco, etc.;

vegetables: solanaceous vegetables (eggplant, tomato, pimento, pepper, potato, etc.), cucurbitaceous vegetables (cucumber, pumpkin, zucchini, water melon, melon, squash, etc.), cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc.), liliaceous vegetables (green onion, onion, garlic, and asparagus), ammiaceous vegetables (carrot, parsley, celery, parsnip, etc.), chenopodiaceous vegetables (spinach, Swiss chard, etc.), lamiaceous vegetables (*Perilla frutescens*, mint, basil, etc.), strawberry, sweet potato, Dioscorea japonica, colocasia, etc.;

flowers;

foliage plants;

turf grasses;

fruits: pomaceous fruits (apple, pear, Japanese pear, Chinese quince, quince, etc.), stone fleshy fruits (peach, plum, nectarine, *Prunus* mume, cherry fruit, apricot, prune, etc.), citrus fruits (*Citrus unshiu*, orange, lemon, rime, grapefruit, etc.), nuts (chestnuts, walnuts, hazelnuts, almond, pistachio, cashew nuts, *macadamia* nuts, etc.), berries (blueberry, cranberry, blackberry, raspberry, etc.), grape, kaki fruit, olive, Japanese plum, banana, coffee, date palm, coconuts, etc.; and trees other than fruit trees; tea, mulberry, flowering plant, roadside trees (ash, birch, dogwood, Eucalyptus, *Ginkgo biloba*, lilac, maple, *Quercus*, poplar, Judas tree, Liquidambar formosana, plane tree, zelkova, Japanese arborvitae, fir wood, hemlock, juniper, *Pinus, Picea*, and Taxus cuspidate), etc.

Particularly, the control method of the present invention can be used to control diseases in agricultural lands for cultivating corn, rice, wheat, barley, sorghum, cotton, soybean, beet, rapeseed, turf grasses or potato.

The aforementioned "plants" include plants, to which resistance to HPPD inhibitors such as isoxaflutole, ALS inhibitors such as imazethapyr or thifensulfuron-methyl, EPSP synthetase inhibitors such as glyphosate, glutamine synthetase inhibitors such as the glufosinate, acetyl-CoA carboxylase inhibitors such as sethoxydim, and herbicides such as bromoxynil, dicamba, 2,4-D, etc. has been conferred by a classical breeding method or genetic engineering technique.

Examples of a "plant" on which resistance has been conferred by a classical breeding method include rape, wheat, sunflower and rice resistant to imidazolinone ALS inhibitory herbicides such as imazethapyr, which are already commercially available under a product name of Clearfield (registered trademark). Similarly, there is soybean on which resistance to sulfonylurea ALS inhibitory herbicides such as thifensulfuron-methyl has been conferred by a classical breeding method, which is already commercially available under a product name of STS soybean. Similarly, examples on which resistance to acetyl-CoA carboxylase inhibitors such as trione oxime or aryloxy phenoxypropionic acid herbicides has been conferred by a classical breeding method include SR corn. The plant on which resistance to acetyl-CoA carboxylase inhibitors has been conferred is described in Proceedings of the National Academy of Sciences of the United States of America (Proc. Natl. Acad. Sci. USA), vol. 87, pp. 7175-7179 (1990). A variation of acetyl-CoA carboxylase resistant to an acetyl-CoA carboxylase inhibitor is reported in Weed Science, vol. 53, pp. 728-746 (2005) and a plant resistant to acetyl-CoA carboxylase inhibitors can be generated by introducing a gene of such an acetyl-CoA carboxylase variation into a plant by genetically engineering technology, or by introducing a variation conferring resistance into a plant acetyl-CoA carboxylase. Furthermore, plants resistant to acetyl-CoA carboxylase inhibitors or ALS inhibitors or the like can be generated by introducing a site-directed amino acid substitution variation into an acetyl-CoA carboxylase gene or the ALS gene of the plant by introduction a nucleic acid into which has been introduced a base substitution variation represented Chimeraplasty Technique (Gura T. 1999. Repairing the Genome's Spelling Mistakes. Science 285: 316-318) into a plant cell.

Examples of a plant on which resistance has been conferred by genetic engineering technology include corn, soybean, cotton, rape, sugar beet resistant to glyphosate, which is already commercially available under a product name of RoundupReady (registered trademark), AgrisureGT, etc. Similarly, there are corn, soybean, cotton and rape which are made resistant to glufosinate by genetic engineering technology, a kind, which is already commercially available under a product name of LibertyLink (registered trademark). A cotton made resistant to bromoxynil by genetic engineering technology is already commercially available under a product name of BXN likewise.

The aforementioned "plants" include genetically engineered crops produced using such genetic engineering techniques, which, for example, are able to synthesize selective toxins as known in genus *Bacillus*.

Examples of toxins expressed in such genetically engineered crops include: insecticidal proteins derived from *Bacillus cereus* or *Bacillus popilliae*; δ-endotoxins such as Cry1Ab, Cry1Ac, Cry1F, Cry1Fa2, Cry2Ab, Cry3A, Cry3Bb1 or Cry9C, derived from *Bacillus thuringiensis*; insecticidal proteins such as VIP1, VIP2, VIP3, or VIP3A; insecticidal proteins derived from nematodes; toxins generated by animals, such as scorpion toxin, spider toxin, bee toxin, or insect-specific neurotoxins; mold fungi toxins; plant lectin; agglutinin; protease inhibitors such as a trypsin inhibitor, a serine protease inhibitor, patatin, cystatin, or a papain inhibitor; ribosome-inactivating proteins (RIP) such as lycine, corn-RIP, abrin, luffin, saporin, or briodin; steroid-metabolizing enzymes such as 3-hydroxysteroid oxidase, ecdysteroid-UDP-glucosyl transferase, or cholesterol oxidase; an ecdysone inhibitor; HMG-COA reductase; ion channel inhibitors such as a sodium channel inhibitor or calcium channel inhibitor; juvenile hormone esterase; a diuretic hormone receptor; stilbene synthase; bibenzyl synthase; chitinase; and glucanase.

Toxins expressed in such genetically engineered crops also include: hybrid toxins of 5-endotoxin proteins such as Cry1Ab, Cry1Ac, Cry1F, Cry1Fa2, Cry2Ab, Cry3A, Cry3Bb1, Cry9C, Cry34Ab or Cry35Ab and insecticidal proteins such as VIP1, VIP2, VIP3 or VIP3A; partially deleted toxins; and modified toxins. Such hybrid toxins are produced from a new combination of the different domains of such proteins, using a genetic engineering technique. As a partially deleted toxin, Cry1Ab comprising a deletion of a portion of an amino acid sequence has been known. A modified toxin is produced by substitution of one or multiple amino acids of natural toxins.

Examples of such toxins and genetically engineered plants capable of synthesizing such toxins are described in EP-A-0 374 753, WO 93/07278, WO 95/34656, EP-A-0 427 529, EP-A-451 878, WO 03/052073, etc.

Toxins contained in such genetically engineered plants are able to confer resistance particularly to insect pests belonging to Coleoptera, Hemiptera, Diptera, Lepidoptera and Nematodes, to the plants.

Genetically engineered plants, which comprise one or multiple insecticidal pest-resistant genes and which express one or multiple toxins, have already been known, and some of such genetically engineered plants have already been on the market. Examples of such genetically engineered plants include YieldGard (registered trademark) (a corn variety for expressing Cry1Ab toxin), YieldGard Rootworm (registered trademark) (a corn variety for expressing Cry3Bb1 toxin), YieldGard Plus (registered trademark) (a corn variety for expressing Cry1Ab and Cry3Bb1 toxins), Herculex I (registered trademark) (a corn variety for expressing phosphinotricine N-acetyl transferase (PAT) so as to confer resistance to Cry1Fa2 toxin and glufosinate), NuCOTN33B (registered trademark) (a cotton variety for expressing Cry1Ac toxin), Bollgard I (registered trademark) (a cotton variety for expressing Cry1Ac toxin), Bollgard II (registered trademark) (a cotton variety for expressing Cry1Ac and Cry2Ab toxins), VIPCOT (registered trademark) (a cotton variety for expressing VIP toxin), NewLeaf (registered trademark) (a potato variety for expressing Cry3A toxin), NatureGard (registered trademark) Agrisure (registered trademark) GT Advantage (GA21 glyphosate-resistant trait), Agrisure (registered trademark) CB Advantage (Bt11 corn borer (CB) trait), and Protecta (registered trademark).

The aforementioned "plants" also include crops produced using a genetic engineering technique, which have ability to generate antipathogenic substances having selective action.

A PR protein and the like have been known as such antipathogenic substances (PRPs, EP-A-0 392 225). Such antipathogenic substances and genetically engineered crops that generate them are described in EP-A-0 392 225, WO 95/33818, EP-A-0 353 191, etc.

Examples of such antipathogenic substances expressed in genetically engineered crops include: ion channel inhibitors such as a sodium channel inhibitor or a calcium channel inhibitor (KP1, KP4 and KP6 toxins, etc., which are produced by viruses, have been known); stilbene synthase; bibenzyl synthase; chitinase; glucanase; a PR protein; and antipathogenic substances generated by microorganisms, such as a peptide antibiotic, an antibiotic having a hetero ring, a protein factor associated with resistance to plant diseases (which is called a plant disease-resistant gene and is described in WO 03/000906). These antipathogenic substances and genetically engineered plants producing such substances are described in EP-A-0392225, WO95/33818, EP-A-0353191, etc.

The "plant" mentioned above includes plants on which advantageous characters such as characters improved in oil stuff ingredients or characters having reinforced amino acid content have been conferred by genetically engineering technology. Examples thereof include VISTIVE (registered trademark) low linolenic soybean having reduced linolenic content) or high-lysine (high-oil) corn (corn with increased lysine or oil content).

Stack varieties are also included in which a plurality of advantageous characters such as the classic herbicide characters mentioned above or herbicide tolerance genes, harmful insect resistance genes, antipathogenic substance producing genes, characters improved in oil stuff ingredients or characters having reinforced amino acid content are combined.

EXAMPLES

While the present invention will be more specifically described by way of formulation examples, seed treatment examples, and test examples in the following, the present invention is not limited to the following examples. In the following examples, the part represents part by weight unless otherwise noted in particular.

The compound (1a) is a compound represented by formula (1) wherein $X^1$ is a methyl group, $X^2$ is a methylamino group, and $X^3$ is a 2,5-dimethylphenyl group and the compound has an R type steric structure according to Cahn-Ingold-Prelog order rule, and represented by the following formula (1a).

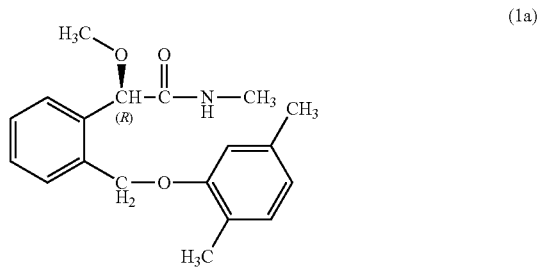

(1a)

The compound (1b) is a compound represented by formula (1), wherein $X^1$ is a methyl group, $X^2$ is a methylamino group, and $X^3$ is a 2,5-dimethylphenyl group and the compound is an racemic body and represented by the following formula (1b).

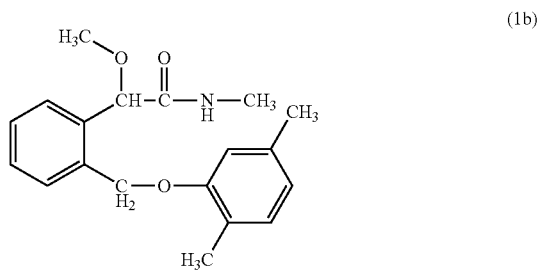 [SMILES: CNC(=O)C(OC)c1ccccc1COc1cc(C)ccc1C]

(1b)

Formulation Example 1

Fully mixed are 2.5 parts of fluoxastrobin, 1.25 parts of the compound I, 14 parts of polyoxyethylene styrylphenyl ether, 6 parts of calcium dodecyl benzene sulfonate and 76.25 parts of xylene, so as to obtain an emulsion.

Formulation Example 2

Five (5) parts of azoxystrobin, 5 parts of the compound I, 35 parts of a mixture of white carbon and a polyoxyethylene alkyl ether sulfate ammonium salt (weight ratio 1:1) and 55 parts of water are mixed, and the mixture is subjected to fine grinding according to a wet grinding method, so as to obtain a flowable formulation.

Formulation Example 3

Five (5) parts of trifloxystrobin, 10 parts of the compound I, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Formulation Example 4

Five (5) parts of the compound (1a) or the compound (1b), 40 parts of the compound I, 5 parts of propylene glycol (manufactured by Nacalai Tesque), 5 parts of SoprophorFLK (manufactured by Rhodia Nikka), 0.2 parts of an anti-form C emulsion (manufactured by Dow Corning), 0.3 parts of proxel GXL (manufactured by Arch Chemicals) and 49.5 parts of ion-exchange water are mixed so as to obtain a bulk slurry. 150 parts of glass beads (diameter=1 mm) are put into 100 parts of the slurry, and the slurry is ground for 2 hours while being cooled with a cooling water. After ground, the resultant is filtered to remove the glass beads and respective flowable formulations are obtained.

Formulation Example 5

Fifty (50) parts of the compound I, 0.5 parts of pyraclostrobin, 38.5 parts of NN kaolin clay (manufactured by Takehara Chemical Industrial), 10 parts of MorwetD425 and 1.5 parts of MorwerEFW (manufactured by Akzo Nobel Corp.) are mixed to obtain an AI premix. This premix is ground with a jet mill so as to obtain a powder formulation.

Formulation Example 6

Four (4) parts of picoxystrobin, 1 part of the compound I, 1 part of synthetic hydrated silicon oxide, 2 parts of calcium lignin sulfonate, 30 parts of bentonite and 62 parts of kaolin clay are fully ground and mixed, and the resultant mixture is added with water and fully kneaded, and then subjected to granulation and drying so as to obtain a granule formulation.

Formulation Example 7

Two (2) parts of orysastrobin, 1 part of the compound I, 87 parts of kaolin clay and 10 parts of talc are fully ground and mixed so as to obtain a powder formulation.

Formulation Example B

Two (2) parts of enestrobin, 20 parts of the compound I, 3 parts of calcium lignin sulfonate, 2 parts of sodium lauryl sulfate and 73 parts of synthetic hydrated silicon oxide are fully ground and mixed so as to obtain wettable powders.

Seed Treatment Example 1

An emulsion prepared as in Formulation example 1 is used for smear treatment in an amount of 500 ml per 100 kg of dried sorghum seeds using a rotary seed treatment machine (seed dresser, produced by Hans-Ulrich Hege GmbH) so as to obtain treated seeds.

Seed Treatment Example 2

A flowable formulation prepared as in Formulation example 2 is used for smear treatment in an amount of 50 ml per 10 kg of dried rape seeds using a rotary seed treatment machine (seed dresser, produced by Hans-Ulrich Hege GmbH) so as to obtain treated seeds.

Seed Treatment Example 3

A flowable formulation prepared as in Formulation example 3 is used for smear treatment in an amount of 40 ml per 10 kg of dried corn seeds using a rotary seed treatment machine (seed dresser, produced by Hans-Ulrich Hege GmbH) so as to obtain treated seeds.

Seed Treatment Example 4

Five (5) parts of a flowable formulation prepared as in Formulation example 4, 5 parts of pigment BPD6135 (manufactured by Sun Chemical) and 35 parts of water are mixed to prepare a mixture. The mixture is used for smear treatment in an amount of 60 ml per 10 kg of dried cotton seeds using a rotary seed treatment machine (seed dresser, produced by Hans-Ulrich Hege GmbH) so as to obtain treated seeds.

Seed Treatment Example 5

A powder agent prepared as in Formulation example 5 is used for powder coating treatment in an amount of 50 g per 10 kg of dried corn seeds so as to obtain treated seeds.

Seed Treatment Example 6

A powder agent prepared as in Formulation example 7 is used for powder coating treatment in an amount of 40 g per 100 kg of dried rice seeds so as to obtain treated seeds.

Seed Treatment Example 7

A flowable formulation prepared as in Formulation example 2 is used for smear treatment in an amount of 50 ml per 10 kg of dried soybean seeds using a rotary seed treatment machine (seed dresser, produced by Hans-Ulrich Hege GmbH) so as to obtain treated seeds.

Seed treatment example 8

A flowable formulation prepared as in Formulation example 3 is used for smear treatment in an amount of 50 ml per 10 kg of dried wheat seeds using a rotary seed treatment machine (seed dresser, produced by Hans-Ulrich Hege GmbH) so as to obtain treated seeds.

Seed Treatment Example 9

Five (5) parts of a flowable formulation prepared as in Formulation example 4, 5 parts of pigment BPD6135 (manufactured by Sun Chemical) and 35 parts of water are mixed and the resultant mixture is used for smear treatment in an amount of 70 ml per 10 kg of potato tuber pieces using a rotary seed treatment machine (seed dresser, produced by Hans-Ulrich Hege GmbH) so as to obtain treated seeds.

Seed Treatment Example 10

Five (5) parts of a flowable formulation prepared as in Formulation example 4, 5 parts of pigment BPD6135 (manufactured by Sun Chemical) and 35 parts of water are mixed and the resultant mixture is used for smear treatment in an amount of 70 ml per 10 kg of sunflower seeds using a rotary seed treatment machine (seed dresser, produced by Hans-Ulrich Hege GmbH) so as to obtain treated seeds.

Seed Treatment Example 11

A powder prepared as in Formulation example 5 is used for powder coating treatment in an amount of 40 g per 10 kg of dried sugar beet seeds so as to obtain treated seeds.

Test Example 1

A DMSO solution of the compound I and a DMSO solution of the compound (1b) were respectively prepared. These solutions were mixed to prepare a DMSO solution containing predetermined concentrations of the compound I and the compound (1b). Ten (10) µL of the DMSO solution and 10 g of seeds of *Pisum sativum* L were mixed by shaking in a 50-ml conical tube and then allowed to stand overnight to prepare treated seeds. A plastic pot was filled with sandy soil and the treated seeds were sown on it and then covered with sandy soil which had been mixed with a bran culture of *Fusarium solani* f. sp. pisi. The sown seeds were watered and then cultured in a greenhouse at 20 to 24° C. After seedlings were emerged, a spore suspension ($1 \times 10^6$/ml) of *Fusarium solani* f. sp. pisi was drenched to the foot of the seedlings and the seedlings were further cultured. After 16 days, the occurrence of pea root rot diseases was checked and the incidence of disease was calculated by Equation 1.

For comparison, a DMSO solution containing a predetermined concentration of the compound (1b) was prepared and subjected to the same test and then the incidence of disease was determined.

In order to calculate a control value, the same test was conducted in which the plants had been treated with none of the test compounds and the incidence of disease was determined.

The control value was calculated by the Equation 2 based on the incidence of disease thus determined.

The results are shown in Table 2.

Incidence of disease=(Number of seedlings in which development of disease was observed)×100/(Total number of sowed seeds)   "Equation 1"

Control value=100×($A-B$)/$A$   "Equation 2"

A: Incidence of disease of plants treated with none of the test compounds

B: Incidence of disease of plants treated with at least one test compound

TABLE 2

| Test compounds | | |
|---|---|---|
| Compound (1b) Active ingredient dosage (g/100 kg seeds) | Compound I Active ingredient dosage (g/100 kg seeds) | Control value |
| 5 | 10 | 82 |
| 1 | 10 | 82 |
| 5 | 0 | 64 |
| 1 | 0 | 64 |

Test Example 2

A plastic pot was filled with sandy soil and seeds of wheat (SHIROGANEKOMUGI) were sown on it, followed by cultivation in a greenhouse for 10 days. A wettable powder of the compound I was prepared by mixing 10 parts of the compound I, 35 parts of a mixture of white carbon and a polyoxyethylene alkyl ether sulfate ammonium salt (weight ratio of 1:1) and 55 parts of water, followed by grinding the mixture. A wettable powder of the compound (1b) was prepared by mixing 10 parts of the compound (1b), 35 parts of a mixture of white carbon and a polyoxyethylene alkyl ether sulfate ammonium salt (weight ratio of 1:1) and 55 parts of water, followed by grinding the mixture. Each of the wettable powder thus prepared was diluted with water, respectively, followed by mixing together to prepare a mixed solution containing predetermined concentrations of the compound I and the compound (1b). The mixed solution was sprayed on leaves of the wheat so that the solution can sufficiently adhere on the surfaces of the wheat leaves. After the spraying followed by air drying, spores of wheat leaf rust mixed with talc were sprayed on the surfaces of the wheat leaves. After allowing to stand overnight at 23° C. under high humidity followed by cultivation in an artificial climate laboratory at 23° C. for 8 days, leaf area and lesion area of the wheat leaves were checked and the incidence of disease was calculated by Equation 3.

For comparison, the wettable powder of the compound (1b) was diluted with water to prepare a solution containing predetermined concentration of the compound (1b) and subjected to the same test to determine the incidence of disease.

In order to calculate a control value, the same test was conducted in which the plants had been treated with none of the test compounds and the incidence of disease was determined.

The control value was calculated by the Equation 2 based on the incidence of disease thus determined.

The results are shown in Table 3.

Incidence of disease=(Lesion area of tested leaves)×100/(Leaf area of tested leaves)       "Equation 3"

TABLE 3

| Test compounds | | |
|---|---|---|
| Compound (1b) Active ingredient concentration (ppm) | Compound I Active ingredient concentration (ppm) | Control value |
| 20 | 200 | 92 |
| 10 | 200 | 83 |
| 20 | 0 | 81 |
| 10 | 0 | 50 |

Test Example 3

A DMSO solution of the compound I, a DMSO solution of the compound (1b), a DMSO solution of kresoxim-methyl, a DMSO solution of pyraclostrobin, a DMSO solution of trifloxystrobin and a DMSO solution of pyribencarb were respectively prepared. These solutions were mixed to prepare a DMSO solution containing predetermined concentrations of the compound I and the compound (1b), a DMSO solution containing predetermined concentrations of the compound I and kresoxim-methyl, a DMSO solution containing predetermined concentrations of the compound I and pyraclostrobin, a DMSO solution containing predetermined concentrations of the compound I and trifloxystrobin and a DMSO solution containing predetermined concentrations of the compound I and pyribencarb. Twenty-five (25) µL of each of the DMSO solution and 10 g of seeds of corn (Pioneer) were mixed by shaking in a 50-ml conical tube and then allowed to stand overnight to prepare treated seeds. A plastic pot was filled with sandy soil and the treated seeds were sown on it and then covered with sandy soil which had been mixed with a bran culture of *Fusarium graminearum*. The sown seeds were watered and then cultured in a greenhouse at 15° C. for 15 days. The number of emerged seedlings was checked and the incidence of disease was calculated by Equation 4.

For comparison, a DMSO solution containing a predetermined concentration of each of the compound (1b), kresoxim-methyl, pyraclostrobin, trifloxystrobin or pyribencarb was prepared respectively and subjected to the same test and then the incidence of disease was determined.

In order to calculate a control value, the same test was conducted in which the plants had been treated with none of the test compounds and the incidence of disease was determined.

The control value was calculated by the Equation 2 based on the incidence of disease thus determined.

The results are shown in Table 4.

Incidence of disease=100×{1−(Number of emerged seedlings)/(Total number of sowed seeds)}       "Equation 4"

TABLE 4

| Test compounds Active ingredient dosage (g/100 kg seeds) | Control value |
|---|---|
| Compound (1b) 10 g + Compound I 50 g | 100 |
| kresoxim-methyl 10 g + Compound I 50 g | 83 |
| pyraclostrobin 10 g + Compound I 50 g | 100 |
| trifloxystrobin 10 g + Compound I 50 g | 100 |
| pyribencarb 10 g + Compound I 50 g | 100 |
| Compound (1b) 10 g | 83 |
| kresoxim-methyl 10 g | 67 |
| pyraclostrobin 10 g | 83 |
| trifloxystrobin 10 g | 83 |
| pyribencarb 10 g | 83 |

Test Example 4

A DMSO solution of the compound I and a DMSO solution of azoxystrobin were respectively prepared. These solutions were mixed to prepare a DMSO solution containing predetermined concentrations of the compound I and azoxystrobin. Twenty-five (25) µL of each of the DMSO solution and 10 g of seeds of corn (Pioneer) were mixed by shaking in a 50-ml conical tube and then allowed to stand overnight to prepare treated seeds. A plastic pot was filled with sandy soil and the treated seeds were sown on it and then covered with sandy soil which had been mixed with a bran culture of *Fusarium avenaceum*. The sown seeds were watered and then cultured in a greenhouse at 15° C. for 15 days. The number of emerged seedlings was checked and the incidence of disease was calculated by Equation 4.

For comparison, a DMSO solution containing a predetermined concentration of azoxystrobin was prepared and subjected to the same test and then the incidence of disease was determined.

In order to calculate a control value, the same test was conducted in which the plants had been treated with none of the test compounds and the incidence of disease was determined.

The control value was calculated by the Equation 2 based on the incidence of disease thus determined.

The results are shown in Table 5.

TABLE 5

| Test compounds<br>Active ingredient dosage<br>(g/100 kg seeds) | Control value |
| --- | --- |
| azoxystrobin 10 g + Compound I 10 g | 83 |
| azoxystrobin 10 g | 67 |

INDUSTRIAL APPLICABILITY

According to the present invention, a composition for controlling plant diseases having high activity, and a method for effectively controlling plant diseases can be provided.

The invention claimed is:

1. A composition for controlling plant diseases comprising, as active ingredients, 4-oxo-4-[(2-phenylethyl)amino]-butyric acid and a quinone outside inhibitor, wherein the quinone outside inhibitor is at least one quinone outside inhibitor selected from the group consisting of azoxystrobin, pyraclostrobin, trifloxystrobin, kresoxim-methyl, pyribencarb and compound (1b):

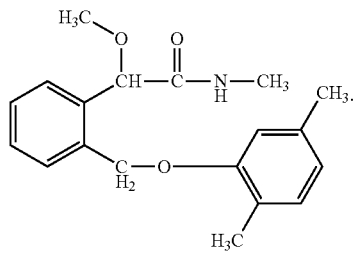

(1b)

2. The composition according to claim 1, wherein a weight ratio of 4-oxo-4-[(2-phenylethyl)amino]-butyric acid to the quinone outside inhibitor is in the range of 0.005:1 to 1000:1.

3. A seed treatment agent comprising, as active ingredients, 4-oxo-4-[(2-phenylethyl)amino]-butyric acid and a quinone outside inhibitor, wherein the quinone outside inhibitor is at least one quinone outside inhibitor selected from the group consisting of azoxystrobin, pyraclostrobin, trifloxystrobin, kresoxim-methyl, pyribencarb and compound (1b):

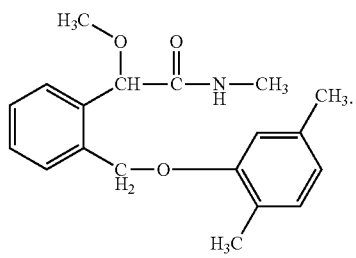

(1b)

4. A plant seed treated with effective amounts of 4-oxo-4-[(2-phenylethyl)amino]-butyric acid and a quinone outside inhibitor, wherein the quinone outside inhibitor is at least one quinone outside inhibitor selected from the group consisting of azoxystrobin, pyraclostrobin, trifloxystrobin, kresoxim-methyl, pyribencarb and compound (1b):

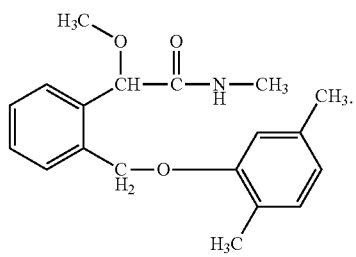

(1b)

5. A method for controlling plant diseases which comprises applying effective amounts of 4-oxo-4-[(2-phenylethyl)amino]-butyric acid and a quinone outside inhibitor to a plant or soil for growing a plant, wherein the quinone outside inhibitor is at least one quinone outside inhibitor selected from the group consisting of azoxystrobin, pyraclostrobin, trifloxystrobin, kresoxim-methyl, pyribencarb and compound (1b):

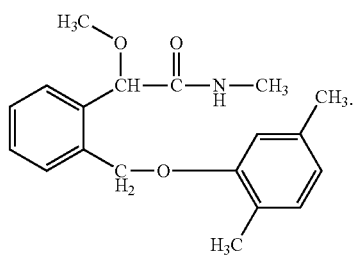

(1b)

* * * * *